United States Patent [19]

Scheiwe et al.

[11] Patent Number: 6,149,942
[45] Date of Patent: Nov. 21, 2000

[54] PHARMACEUTICAL PELLET FORMULATION

[75] Inventors: Max Werner Scheiwe, Maulburg, Germany; Thomas Villiger, Muttenz, Switzerland

[73] Assignee: Melpha AG, Aesch, Switzerland

[21] Appl. No.: 08/952,618

[22] PCT Filed: May 24, 1996

[86] PCT No.: PCT/CH96/00203

§ 371 Date: Jan. 9, 1998

§ 102(e) Date: Jan. 9, 1998

[87] PCT Pub. No.: WO96/37195

PCT Pub. Date: Nov. 28, 1996

[30] Foreign Application Priority Data

May 24, 1995 [CH] Switzerland ............................ 1542/95

[51] Int. Cl.[7] ................................ A61K 9/58; A61K 9/62
[52] U.S. Cl. ........................... 424/490; 497/499; 497/497
[58] Field of Search ..................................... 424/489, 490, 424/473, 497, 470, 499, 451, 469, 475; 514/53

[56] References Cited

U.S. PATENT DOCUMENTS

| | | | |
|---|---|---|---|
| 5,045,321 | 9/1991 | Makino et al. | 424/475 |
| 5,538,954 | 7/1996 | Koch et al. | 514/53 |
| 5,869,097 | 2/1999 | Wong et al. | 424/473 |

FOREIGN PATENT DOCUMENTS 0526862  2/1996  European Pat. Off. .

*Primary Examiner*—Thurman K. Page
*Assistant Examiner*—Blessing Fubara
*Attorney, Agent, or Firm*—Ladas & Parry

[57] ABSTRACT

A pharmaceutical pellet formulation having a core containing omeprazole as an active ingredient, and also having an outer, enteric coating encasing the core. Titanium dioxide is added to the core, and optionally, to the enteric coating in order to retard decomposition of the omeprazole resulting from the action of penetrating moisture and solvents, thus greatly improving the storage stability of the omeprazole formulation.

14 Claims, No Drawings

PHARMACEUTICAL PELLET FORMULATION

This application is a 372 of PCT/CH/96/00203 filed May 24, 1996.

The invention relates to a novel stable pharmaceutical pellet formulation containing omeprazole and to a process for the preparation of this formulation.

The pharmaceutical effects of omeprazole on the organism has been extensively researched and are widely known. On the other hand, the longer-term stability of pharmaceutical formulations containing omeprazole has so far proved troublesome. Because the stability of omeprazole is influenced by organic solvents and moisture and its conversion is promoted by reagents giving an acid reaction or hindered by reagents giving an alkaline reaction, an oral omeprazole formulation must be protected with an enteric coating against the action of stomach acid so that it can develop its effect in the small intestine.

Conventionally, however, enteric coatings contain components giving a acid reaction, so, in contact therewith, omeprazole would be continuously decomposed and hence, over time, would change its appearance as well as lose its effect.

To reduce these disadvantages, attempts have been made e.g. to provide pharmaceutical omeprazole formulations with two coatings, the inner coating being intended to form a barrier against the outer, enteric coating which decomposes the omeprazole, and against penetrating moisture.

It has been found, however, that the stability of such pharmaceutical formulations still does not satisfy the desired criteria and that coating the formulation twice greatly increases the cost of the manufacturing process.

The object of the present invention is therefore to provide a stable pharmaceutical formulation with a core containing omeprazole as the active ingredient, and a single coating, which formulation avoids the above-mentioned disadvantages.

Surprisingly, it has now been found that the addition of $TiO_2$ to the core and optionally to the enteric coating greatly improves the storage stability of the omeprazole formulation according to the invention compared with formulations of the state of the art, and that the use of a separate intermediate layer acting as a barrier can thereby be avoided.

The above object is therefore achieved by the provision of a pharmaceutical pellet formulation with a core containing omeprazole in the form of its free base as the active ingredient, and with an enteric coating, in which formulation the core and optionally the coating contain $TiO_2$ and other adjuncts.

Examples of suitable adjuncts for the pellet formulation according to the invention are binders, sedimentation retarders and pH correctors.

The active ingredient omeprazole is used in the form of its free base. Either the omeprazole is used as starter cores in the form of coarse crystals, preferably in the particle size range 0.2–0.5 mm or 0.4–1 mm, or the omeprazole in the form of fine crystals (e.g. <50 micrometers or <10 micrometers) or coarse crystals (e.g. <250 micrometers), in a suspension with adjuncts, is applied to starter cores, e.g. consisting of sugar (sucrose), which optionally contain additives such as sodium a carboxymethyl starch, polyvinylpyrrolidone, gelatine or other compounds known to those skilled in the art.

The suspension or solution applied to the starter cores contains omeprazole and adjuncts, especially at least one binder, at least one sedimentation retarder, pH correctors and optionally at least one dyestuff and/or pigment and/or lake, lubricants/antiadhesive agents and suspension stabilizers/thickeners, and $TiO_2$ as a stabilizer for improving the storage stability, in water or a mixture of water and one or more conventional organic solvents, or in an organic solvent.

Examples of suitable binders are sodium carboxymethyl starch, polyvinylpyrrolidone, gelatine, hydroxypropyl methyl cellulose, hydroxyethyl cellulose, xanthan, carrageenan products, polyvinyl acetate, sodium carboxymethyl cellulose, ethyl cellulose, starch mucilage or liquefied waxes, either individually or in combination with one another.

Examples of suitable sedimentation retarders are highly disperse silicon dioxide, starch mucilage, mucilages like tragacanth, gums, e.g. gum arabic, xanthans, aliginates or carrageenan products, either on their own or in combination with one another.

Examples of suitable pH correctors are sodium hydroxide, hydrochloric acid, methylglucamine or buffer substances like sodium dihydrogen phosphate or disodium hydrogen phosphate.

Examples of dyestuffs, pigments or lakes which can be used as iron oxides, erythrosine, yellow orange S, tartraziane or indigotin.

Talcum is a particularly suitable lubricant/antiadhesive agent and highly disperse silicon dioxide is a particularly suitable suspension stabilizer/thickener.

The core of a pharmaceutical formulation according to the invention contains omeprazole in an amount of 20–70% by weight, preferably 30–50% by weight, and adjuncts and $TiO_2$ in an amount of 80–30% by weight, preferably 70–50% by weight, based in each case on the core of the pellet and deducting the weight of the starter cores.

$TiO_2$ is present here in an amount of about 5–40% by weight, preferably 10–30% by weight, based on omeprazole.

The suspension I, containing omeprazole and $TiO_2$, together with the suspension II, optionally containing $TiO_2$, can be applied to the starter cores by a gradient spraying process. This process begins with application of the suspension I to the starter cores, after which the high proportion of suspension I is reduced continuously or batchwise, e.g., by dilution with the suspension II, to the point where the suspension or solution contains practically no more omeprazole at the end of this process step.

After application of the suspensions I and II, the pellets are dried inside or outside the coating unit. The drying can be effected by exposure to a gas, direct contact with heat, microwave radiation or infrared radiation, with or without a vacuum.

After the pellets have been dried, an enteric lacquer is applied to prevent decomposition of the pellets in the gastric juice. The lacquer is applied e.g. in the form of a suspension in water or a mixture of water and an organic solvent. It contains film-forming agents and optionally binders, sedimentation retarders, pH correctors and optionally plasticizers and/or dyestuffs, pigments or lakes.

Alternatively the process can also be carried out in such a way that the suspension I, containing omeprazole and $TiO_2$, is applied to the starter cores and dried, and only then is the suspension II applied to the pellets, preferably by means of a gradient spraying process, in combination with the enteric lacquer.

If the enteric lacquer is applied in combination with $TiO_2$, the amount of $TiO_2$ used is approximately in the range 5–30% by weight, preferably 10–20% by weight, based on omeprazole.

If $TiO_2$ is also used in the coating, the total amount of $TiO_2$ in the core and in the coating is about 10–40% by weight, preferably about 25–35% by weight, based on omeprazole.

Examples of suitable film-forming agents are ethyl cellulose, cellulose acetate-phthalate, poly(methacrylic acid-methyl methacrylate).

Examples of suitable binders are sodium carboxymethyl starch, polyvinylpyrrolidone, gelatine, hydroxypropyl methyl cellulose, hydroxyethyl cellulose, xanthan, carrageenan products, polyvinyl acetate, sodium carboxymethyl celluose, ethyl cellulose, starch mucilage or liquefied waxes, either individually or in combination with one another.

Examples of suitable sedimentation retarders are highly disperse silicon dioxide, starch mucilage, mucilages like tragacanth, gums, e.g. gum arabic, xanthans, alginates or carrageenan products, either on their own or in combination with one another.

Examples of suitable pH correctors are sodium hydroxide, methylglucamine, hydrochloric acid or buffer substances like sodium dihydrogen phosphate or disodium hydrogen phosphate.

Examples of suitable plasticizers are citric acid esters like triethyl citrate, glycerol derivatives like glycerol triacetate, salts of long-chain fatty acids like magnesium stearate, polywaxes like polyethylene glycol, and/or phthalates like dibutyl phthalate.

Examples of dyestuffs, pigments or lakes which can be used are iron oxides, erythrosine, yellow orange S, tartrazine or indigotin.

The amount of lacquer used is about 15–80% by weight of the core (incl. starter cores).

The pellets coated with an enteric film are produced e.g. by the pan process, by the drum coater process or, preferably, by the fluidized bed process (e.g. using a Hüttlin spherical coater, an Aeromaic, a Glat or the like).

In the pan process, the starter cores are heated in the pan, e.g. a coating pan of bulb-shaped cross-section, by means of wall heating or warm gas blasted in directly, e.g. through a dip tube, perforated hollow lance or other tube, and then, with the pan rotating and with appropriate continuous heating, are sprayed with the suspensions or solutions.

The drum coater process is analogous to the pan process, except that the starter cores are placed in a perforated drum, where they are heated and sprayed.

In the fluidized bed process, the starter cores are placed in a fluidized bed unit, for example of the Aeromatic, Glatt or Hüttlin spherical coater type, or the like, heated with the air or gas of the fluidized bed and then sprayed with the suspensions or solutions while swirling continues. In the spraying process, the nozzle or nozzles are located above the swirling material; in the under-bed process, the nozzle is arranged under the fluidized bed. The nozzle sprays in the direction of flow of the gas in the co-current process and in the opposite direction in the counter-current process.

After drying in the coating unit or in a separate drying unit, the enteric lacquer, either on its own or in combination with the suspension containing $TiO_2$, is sprayed on in a unit, as described above, the coated pellets are then dried and the undersized or oversized particles are removed from the appropriately sized pellets by sieving or pneumatic classification.

The invention will now be illustrated in greater detail with the aid of the Examples.

EXAMPLE 1

In a fluidized bed apparatus (Aeromatic) with warm incoming air, 700 g of sugar pellets are sprayed with a suspension I containing 37.5 g of hydroxypropyl methyl cellulose, 15 g of titanium dioxide, 18.75 g of disodium hydrogen phosphate, 3.75 g of highly disperse silicon dioxide and 100 g of omeprazole in 375 g of water. While the sugar pellets are being sprayed with the suspension I, a suspension II, consisting of 75 g of hydroxypropyl methyl cellulose, 11.25 g of highly disperse silicon dioxide, 18.75 g of disodium hydrogen phosphate and 15 g of titanium dioxide in 1125 g of water, is gradually added to the suspension I and spraying is continued until the suspensions I and II have been completely used up. The pellets are then dried with warm air and an enteric lacquer, consisting of 150 g of poly(methacrylic acid/methyl methacrylate), 20 g of triethyl citrate, 15 g of talcum and 10 g of titanium dioxide in 1000 g of water, is applied. The resulting pellets are subsequently dried to equilibrium moisture content at 48° C. in the fluidized bed and then filled into capsule sin conventional manner.

EXAMPLE 2

In a fluidized bed apparatus with warm incoming air, 420 g of sugar pellets are sprayed with a suspension I containing 66 g of omeprazole, 37.5 g of methyl hydroxypropyl cellulose, 22.5 g of disodium hydrogen phosphate, 4.5 g of highly disperse silicon dioxide and 13.5 g of titanium dioxide in water. When the application is complete, the pellets are dried.

The dried pellets are then coated in the above fluidized bed apparatus with a suspension II consisting of 25 g of methyl hydroxypropyl cellulose, 8.8 g of titanium dioxide, 7.5 g of highly disperse silicon dioxide and hydrochloric acid (to adjust the pH to 4.0) in 450 g of purified water, a suspension III, consisting of 250 g of Eudragit L30D and 10 g of triethyl citrate in 250 g of purified water, slowly being mixed into the suspension II, with stirring. When the application is complete, the pellets are dried and filled into capsules in conventional manner.

EXAMPLE 3

In a fluidized bed apparatus with warm incoming air, 315 g of sugar pellets are sprayed with a suspension I containing 45 of omeprazole, 33.8 g of methyl hydroxypropyl cellulose, 9 g of methylglucamine, 4.5 g of titanium dioxide and 2 g of highly disperse silicon dioxide in 360 g of purified water. When the application is complete, the pellets are dried and then processed further according to Example 2.

EXAMPLE 4

The stability of omeprazole pellets prepared according to Example 1 was compared with analogous omeprazole pellets commercially available under the trademarks ANTRA and SOFEXOL.

In each case the white pellets were packed in hard gelatine capsules and the capsules in brown PE bottles. The preparations were kept for 6 months at temperatures of 21–25° C. (room temperature), 31° C. (drying cabinet), 41° C. (drying cabinet) and 40° C. (drying cabinet; relative humidity 75%) and tested for their stability.

This test showed that the 3 products remained approximately unchanged in terms of their omeprazole content at storage temperatures of 21–25° C. 31° C. and 41° C.; in the case of the ANTRA product, the pellets exhibited slight yellowish discolourations after storage for 6 months at 31° C. and even at room temperature, and in the case of SOFEXOL, the pellets exhibited yellow-brown discolourations after storage for 6 months at a temperature of 31° C., whereas storage of the product according to the invention for 6 months produced discolourations only at 41° C.

However, significant differences in omeprazole content were found between the pellets according to the invention, on the one hand, and ANTRA and SOFEXOL, on the other, at a storage temperature of 40° C. and a relative humidity of 75. The data are presented in FIG. 1 for clarification. The omeprazole content of a capsule was measured in each case. It can be concluded from these measurements that the product according to the invention is appreciably more stable than the two reference products.

What is claimed is:

1. A pharmaceutical pellet formulation with a core containing omeprazole in the form of its free base as the active ingredient, and an enteric coating, the core and, optionally, the coating contain $TiO_2$.

2. The pharmaceutical formulation of claim 1, wherein the adjuncts used are binders, sedimentation retarders and pH correctors.

3. The pharmaceutical formulation of claim 1, wherein $TiO_2$ is present in the core in an amount of 5–40% by weight, preferably about 10–30% by weight, based on omeprazole.

4. The pharmaceutical formulation of claim 1, wherein $TiO_2$ is present in the core and coating in an amount of 10–40% by weight based on omeprazole.

5. The pharmaceutical formulation of claim 1, wherein omeprazole is present in the core in an amount of 20–70% by weight and adjuncts and $TiO_2$ are present in the core in an amount of 80–30% by weight, based in each case on the weight of the core without starter cores.

6. The pharmaceutical formulation of claim 1, wherein omeprazole is present in the core in an amount of 30–50% by weight and adjuncts and $TiO_2$ are present in the core in an amount of 70–50% by weight, based in each case on the weight of the core without starter cores.

7. The pharmaceutical formulation of claim 1, wherein the coating makes up 15–80% by weight based on the weight of the core.

8. The pharmaceutical formulation of claim 1, wherein the binder used is hydroxypropyl methyl cellulose.

9. The pharmaceutical formulation of claim 1, wherein the sedimentation retarder used is highly disperse silicon dioxide.

10. The pharmaceutical formulation of claim 1, wherein the pH corrector used is disodium hydrogen phosphate or methylglucamine.

11. The pharmaceutical formulation of claim 1, wherein the enteric coating contains poly(methacrylic acid/methyl methacrylate), triethyl citrate, talcum and optionally titanium dioxide.

12. A method for the preparation of a pharmaceutical formulation with a core containing omeprazole in the form of its free base as the active ingredient, and an enteric coating, the core and, optionally, the coating contain $TiO_2$, wherein initially a suspension I, containing a high proportion of omeprazole, is applied with adjuncts and $TiO_2$ to starter cores, the high proportion of omeprazole in the suspension is then reduced continuously or batchwise by dilution of the suspension to be sprayed with a solution or suspension II of adjuncts, optionally with $TiO_2$ to the point where the mixture of suspensions I and II to be applied contains practically no more omeprazole at the end of this process step, and the resulting pellets are then dried and provided with an enteric coating.

13. A method for the preparation of a pharmaceutical formulation with a core containing omeprazole in the form of its free base as the active ingredient, and an enteric coating, the core and, optionally, the coating containing $TiO_2$, wherein a suspension I containing omeprazole is applied with adjuncts and $TiO_2$ to starter cores, and the resulting pellets are then dried and a suspension II containing $TiO_2$ is then applied, together with an enteric coating.

14. The pharmaceutical formulation of claim 4 wherein the $TiO_2$ is present in the core and coating in an amount from 25–35% by weight based on omeprazole.

* * * * *

UNITED STATES PATENT AND TRADEMARK OFFICE
CERTIFICATE OF CORRECTION

PATENT NO. : 6,149,942
DATED : November 21, 2000
INVENTOR(S) : Max Werner Scheiwe et al.

It is certified that error appears in the above-identified patent and that said Letters Patent is hereby corrected as shown below:

<u>Title page,</u>
Item [73], delete "Melpha AG" and insert -- Mepha AG --

Signed and Sealed this

Eleventh Day of June, 2002

*Attest:*

*Attesting Officer*

JAMES E. ROGAN
*Director of the United States Patent and Trademark Office*